(12) United States Patent
Laikhter et al.

(10) Patent No.: US 8,530,634 B2
(45) Date of Patent: Sep. 10, 2013

(54) METHOD OF OLIGONUCLEOTIDE LABELING USING CYCLOADDITION REACTION

(75) Inventors: Andrei Laikhter, Lexington, MA (US); Suresh C. Srivastava, Burlington, MA (US); Naveen P. Srivastava, Burlington, MA (US)

(73) Assignee: ChemGenes Corporation, Wilmington, MA (US)

( * ) Notice: Subject to any disclaimer, the term of this patent is extended or adjusted under 35 U.S.C. 154(b) by 128 days.

(21) Appl. No.: 13/318,587

(22) PCT Filed: May 5, 2010

(86) PCT No.: PCT/US2010/033701
§ 371 (c)(1), (2), (4) Date: Nov. 2, 2011

(87) PCT Pub. No.: WO2010/129656
PCT Pub. Date: Nov. 11, 2010

(65) Prior Publication Data
US 2012/0058476 A1    Mar. 8, 2012

Related U.S. Application Data

(60) Provisional application No. 61/215,339, filed on May 5, 2009.

(51) Int. Cl.
*C07H 21/02* (2006.01)
*C07H 21/04* (2006.01)
*C12Q 1/68* (2006.01)

(52) U.S. Cl.
USPC .................. 536/23.1; 536/26.6; 435/6.1

(58) Field of Classification Search
USPC .................. 536/26.6, 23.1; 435/6.1
See application file for complete search history.

(56) References Cited

U.S. PATENT DOCUMENTS

| | | | |
|---|---|---|---|
| 5,744,595 | A | 4/1998 | Srivastava et al. |
| 6,015,886 | A | 1/2000 | Dale et al. |
| 2007/0099222 | A1 | 5/2007 | Gee et al. |
| 2008/0050731 | A1 | 2/2008 | Agnew et al. |

OTHER PUBLICATIONS

Notification of Transmittal of the International Search Report and Written Opinion of the International Searching Authority from counterpart International Application No. PCT/US2010/033701, dated Jan. 27, 2011.
Notification Concerning Transmittal of International Preliminary Report on Patentability for International Application No. PCT/US2010/033701 dated Nov. 9, 2011.

*Primary Examiner* — Jezia Riley
(74) *Attorney, Agent, or Firm* — Hamilton, Brook, Smith & Reynolds, P.C.

(57) ABSTRACT

The invention provides a novel method of labeling oligonucleotides, with reporter moieties, including but not limited to, quenchers, fluorophores, biotin, digoxigenin, peptides and proteins. In addition, this invention provides a method of detecting hybridization of oligonucleotides. This invention also provides novel azo quenchers having the general formula shown below. The invention further provides compositions comprising labeled oligonucleotides and solid supports. The invention also provides kits comprising at least one composition of the present invention.

21 Claims, 1 Drawing Sheet

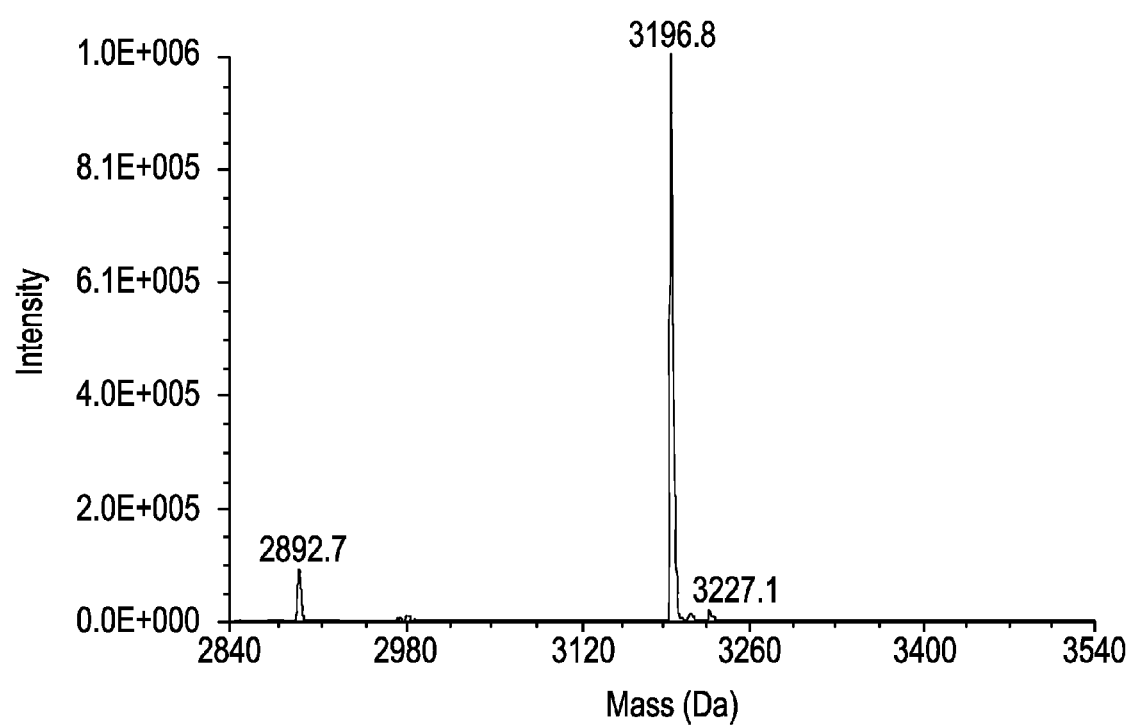

METHOD OF OLIGONUCLEOTIDE LABELING USING CYCLOADDITION REACTION

RELATED APPLICATION

This application is the U.S. National Stage of International Application No. PCT/US2010/033701, filed May 5, 2010, which designates the U.S., published in English, and claims the benefit of U.S. Provisional Application No. 61/215,399, filed May 5, 2009. The entire teachings of the above applications are incorporated herein by reference.

INCORPORATION BY REFERENCE OF MATERIAL IN ASCII TEXT FILE

This application incorporates by reference the Sequence Listing contained in the following ASCII text file, filed concurrently herewith:

File name: 44411000002SeqList.txt; created Nov. 2, 2011, 2.14 KB in size.

BACKGROUND OF THE INVENTION

Oligonucleotides are often modified or labeled with reporter moieties such as quenchers, fluorophores, biotin, etc. These labeled oligonucleotides can provide information regarding binding and other biological phenomena, the structure of DNA, the association of macromolecules, and the size and mobility of protein and DNA complexes.

Several attachment chemistries are currently used for modifying oligonucleotides. For example, primary amino groups are widely used to attach modifiers, reporter moieties or labels to an oligonucleotide. In addition, they can be used to attach an oligonucleotide to a solid surface.

Cycloaddition reaction has been used for the synthesis of labeled oligonucleotides. (Agnew, B. et al, US patent application 20080050731/A1, which is incorporated herein by reference). The methods have been limited to the post-synthetic attachment of labels, and the proposed methods have not been commercially viable alternatives to standard synthesis approaches. Previously described post-synthetic methods permit the incorporation of only a single type of reporter moiety or multiple copies of the same reporter moiety into an oligonucleotide.

Labeled oligonucleotides have a wide variety of useful applications. For example, light quenching processes that rely on the interaction of a fluorophore and quencher as their spatial relationship changes can be used in convenient processes for detecting and/or identifying oligonucleotides and other biological phenomena. In one such method, the change in fluorescence of a fluorophore or quencher can be monitored as two oligonucleotides (one containing a fluorophore and one containing a quencher) hybridize to each other. The hybridization can be detected without intervening purification steps that separate unhybridized from hybridized oligonucleotides. Currently, quencher groups are commonly placed at the end of a probe sequence while the fluorophore is placed at the opposite end, solely for ease of synthesis. However, in some applications, such as real-time PCR, dual-labeled probes are more effective when the labels are placed closer to each other.

Perhaps the most common mechanism of fluorescent quenching is fluorescent resonance energy transfer ("FRET"). For FRET to occur, a fluorophore and a fluorescent quencher must be within a suitable distance for the quencher to absorb energy from the donor. In addition, there must be overlap between the emission spectrum of the fluorescent donor and the absorbance spectrum of the quencher. This requirement complicates the design of probes that utilize FRET because not all potential quencher/fluorophore pairs can be used. For example, the quencher known as BHQ-1, which absorbs light in the wavelength range of about 520-550 nm, can quench the fluorescent light emitted from the fluorophore, fluorescein, which fluoresces maximally at about 520 nm. In contrast, the quencher BHQ-3, which absorbs light in the wavelength range of about 650-700 nm would be almost completely ineffective at quenching the fluorescence of fluorescein through FRET but would be quite effective at quenching the fluorescence of the fluorophore known as Cy5 which fluoresces at about 670 nm.

Oligonucleotides labeled with fluorophores and quenchers can also be used to monitor the kinetics of PCR amplification. For example, a PCR reaction is performed using oligonucleotides designed to hybridize to the 3' side ("downstream") of an amplification primer so that the 5'-3' exonuclease activity of a polymerase digests the 5' end of the probe, cleaving off one of the dyes. The fluorescence intensity of the sample increases and can be monitored as the probe is digested during the course of amplification.

Similar oligonucleotide compositions may be used in other molecular/cellular biology and diagnostic assays, such as end-point PCR, in situ hybridizations, in vivo DNA and RNA species detection, single nucleotide polymorphism (SNPs) analysis, enzyme assays, and in vivo and in vitro whole cell assays.

SUMMARY OF THE INVENTION

The invention provides a method for linking a reporter molecule to an oligonucleotide comprising a reacting reporter molecule having an aliphatic azide moiety with an alkyne substituted reactant coupled to a solid support to form a triazole linker between the reporter moiety and the reactant. The reporter moieties include, but are not limited to, quenchers, fluorophores, biotin, digoxigenin, peptides and proteins. The invention also provides an oligonucleotide labeled with at least two different reporter moieties.

This invention further provides novel azo quenchers having the general formula shown below in Formula 3: Each of $R_{1-4}$ is individually selected from the group consisting of hydrogen; electron withdrawing groups such as halogens, CN, CNS, keto, alkoxy groups; alkyl groups; aryl groups; and heteroaryl groups. Suitable substituents include electron withdrawing groups, such as those described above.

In addition, this invention provides an oligonucleotide labeled with the novel quencher as well as a method of detecting hybridization of oligonucleotides using the labeled oligonucleotide.

The invention provides compositions comprising a quencher linked to a compound selected from the group consisting of an antigen, a steroid, a vitamin, a drug, a hapten, a metabolite, a toxin, an environmental pollutant, an amino acid, a protein, a carbohydrate, a solid support, a linker, and a lipid, wherein the quencher is attached to the compound via cycloaddition reaction. The invention further provides compositions comprising labeled oligonucleotides and solid supports. The invention also provides kits comprising at least one composition of the present invention.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1 is an ESI Mass spectrum of oligonucleotide SEQ ID NO 1.

DETAILED DESCRIPTION OF THE INVENTION

The invention provides a novel method of labeling oligonucleotides with reporter moieties during synthesis of the oligonucleotide. The method permits the attachment of several different reporter moieties to a single oligonucleotide at specified position in the sequence of the oligonucleotide.

For the purposes of this invention, the term "reporter moiety" refers to a substituent that allows detection, either directly or indirectly, of a compound at low concentrations. Suitable reporter moieties include, but are not limited to, enzymes (such as horseradish peroxidase, alkaline phosphatase, beta-galactosidase or glucose-6-phosphate dehydrogenase), which produce a signal detectable, for example, by colorimetry, fluorescence or luminescence; chromophores, such as fluorescent, luminescent or dye compounds; groups with an electron density which can be detected by electron microscopy or through their electrical property, such as by conductivity, amperometry, voltametry, or impedance measurements; and groups which can be detected using optical methods, such as diffraction, surface plasma resonance or contact angle variation, or physical methods, such as atomic force spectroscopy, or the tunnel effect. Other suitable reporter moieties include, but are not limited to, biotin, digoxigenin, peptides, proteins, antibodies, glycoproteins, and sugars.

In one embodiment, the method comprises cycloaddition reaction between a reporter moiety having an alkyl azide and alkyne group forming a triazole heterocycle. The triazole linker is completely orthogonal to reactions during phosphoramidite oligonucleotide synthetic cycle and can be used as a universal method for introduction of multiple modifications into an oligonucleotide. The cycloaddition reaction can be used to introduce almost any modification into an oligonucleotide during synthesis or prior to synthesis by modification of the solid support. The triazole linker is remarkably stable, and remains intact during oligonucleotide processing. This method also permits the introduction of multiple different reporter moieties into an oligonucleotide at specified positions in the sequence.

The 2'-alkynyl modified nucleoside phosphoramidites (Formula 1) and solid supports have been described previously (Srivastava, S., et al. U.S. Pat. No. 5,744,595, the entire teachings of which are incorporated herein by reference). Those nucleosides can be linked to a solid support, a 2'-alkynyl modified nucleoside phosphoramidites, or a composition of Formula 2: wherein lcaa is a linker used to attach an oligonucleotide to a solid support during synthesis of the oligonucleotide, such as long chain $C_{12}$-$C_{24}$ carboxylic amino acids attached to controlled pore glass (CPG) or polystyrene.

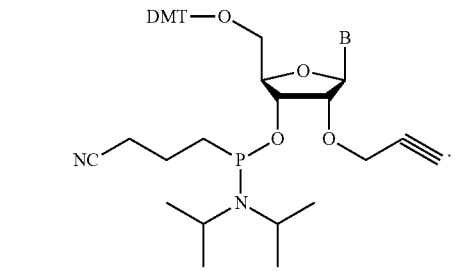

Formula 1

Where B = A (N—Bz), C (N—Bz), C (N—Ac), G (N-iBu), (Bz is benzoyl; Ac is aceyl, and iBu is iso-butyryl).

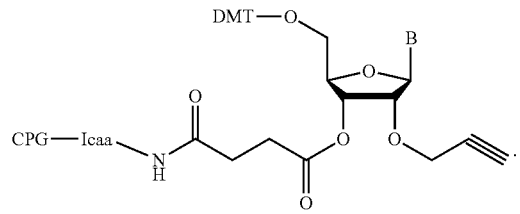

Formula 2

Where B = A (N—Bz), C (N—Bz), C (N—Ac), G (N-iBu),

The 2'-alkynyl modified oligonucleotides, 2'-alkynyl modified nucleosides, and 2'-alkynyl modified nucleoside phosphoramidites for use in the present invention include those containing the traditional nucleobases, such as adenine, guanine, cytosine, uracil and thymine, and those containing modified nucleobases. Examples of modified nucleobases include Hypoxanthyl, 2-aminopurinyl, 2,6-diaminopurinyl, pseudouracyl, 5-Fluoro-Uracyl, 5-fluoro-Cytosyl, 5-methyl-Uracyl, 5-methyl-Cytosyl, 5-bromo-Uracyl, 5-bromo-Cytosyl, 5-iodo-Uracyl, 5-vinyl-Uracyl, $N^3$-methyl-Uracyl, $N^3$-methyl-Cytosyl, $N^3$-methyl-thyminyl, 4-thio-Uracyl, 8-bromo-Adenyl, 8-oxo-Adenyl, 8-oxo-Guanyl, 8-oxo-Hypoxanthyl, 8-bromo-Hypoxanthyl, $N^1$-methyl-Adenyl, $N^1$-methyl-Hypoxanthyl, $N^1$-methyl-Guanyl, etheno-Adenyl and etheno-Cytosyl.

The term "solid support" refers to any support that is compatible with oligonucleotide synthesis. For example, the following are suitable: glass, controlled pore glass (CPG), polymeric materials, polystyrene beads, coated glass, and the like.

"Alkyl" means straight chained or branched hydrocarbon. Typically, an alkyl group is $C_1$-$C_{10}$, more commonly $C_1$-$C_6$. Examples include methyl, ethyl, i-propyl, propyl, n-butyl, sec-butyl and tert-butyl.

"Aliphatic" means a straight or branched linear or cyclic hydrocarbon chain. Aliphatic groups may include diradicals such as alkylene, alkenylene, or alkynylene hydrocarbon chains. Carbon atoms within the aliphatic group may be substituted with heteroatoms such as oxygen, nitrogen or sulfur. For example, carbon atoms within a carbon chain could be substituted with oxygen atoms to form a polyethylene glycol chain.

Alkylene groups are diradicals and are saturated hydrocarbon chains without double or triple bonds, for example, —$CH_2CH_2CH_2$—. Alkenylene groups are diradicals and are unsaturated hydrocarbon chains that include at least one double bond, for example, —CH=CH—$CH_2$—. Alkynylene groups are diradicals and are unsaturated hydrocarbon chains that include at least one triple bond, for example, —C≡C—CH$_2$—. A hydrocarbon group may also include a double and triple bond simultaneously.

A "linker" is a diradicals that attaches to two different groups. For example, —CH$_2$CH$_2$CH$_2$— is an aliphatic linker because it would attach to another moiety at both ends.

"Alcohol protecting group" is, for example, trityl, dimethoxytrityl, monomethoxytrityl, tert-butyldimethylsilyl or 2-(2-nitrophenyl)propoxycarbonyl.

"Keto" means a compound of the structural formula C(=O)C$_1$-C$_{20}$ alkyl. The term "aryl" as used herein refers to cyclic aromatic carbon chain having twenty or fewer carbon atoms, e.g., phenyl, naphthyl, biphenyl, and anthracenyl. One or more carbon atoms of the aryl group may also be substituted with, e.g., alkyl; aryl; heteroaryl; a halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl, or arylalkylaminocarbonyl; carboxyl, or alkyl- or aryloxycarbonyl; aldehyde; aryl- or alkylcarbonyl; iminyl, or aryl- or alkyliminyl; sulfo; alkyl- or alkylcarbonyl; iminyl, or aryl- or alkyliminyl; sulfo; alkyl- or arylsulfonyl; hydroximinyl, or aryl- or alkoximinyl.

The term "heteroaryl" refers to aryl groups (or rings) that contain from one to four heteroatoms selected from N, O, S, and Se, wherein the nitrogen, sulfur, and selenium atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents heteroaryl ring systems are as described above for aryl.

The term "labeling efficiency" means mole percent of the oligonucleotides that are labeled at the designated position or oligonucleotide. For example, if the labeling efficiency at a particular nucleotide in an oligonucleotide is 90%, than at least 90 mol % of the oligonucleotides are labeled at the position with the designated reporter or propargyl group. In the oligonucleotides described herein, the labeling efficiency at each nucleotide designated as labeled is at least 90%, preferably at least 95%, more preferably at least 99%.

The term "labeled" means a that group normally present in the ribosyl ring of a naturally occurring or synthetic nucleotide is replaced with a another functional group. For example, the oligonucleotides disclosed herein are commonly labeled by replacing the hydroxyl group at the 2 position of a ribosyl ring in one or more designated nucleotides with a propargyl group or a reporter group.

In another embodiment, the method permits incorporation of an alkynyl-substituted nucleotide into an oligonucleotide followed by reaction with a reporter moiety having an azide substituent capable of forming a triazole heterocycle with the alkynyl group (Scheme 1). Suitable conditions for this reaction are provided in U.S. Published Application No. 2008/0050731, the entire teachings of which are incorporated herein by reference. The reporter moiety can be added immediately after the alkynyl-substituted nucleotide is added to the oligonucleotide or the reporter moiety can be added after additional nucleotides or alkynyl-substituted nucleotides have been added to the oligonucleotide. In another suitable embodiment, the novel method permits internal incorporation of a reporter moiety into an oligonucleotide as a reporter moiety substituted nucleotide which is incorporated into the oligonucleotide using standard phosphoramidite chemistry.

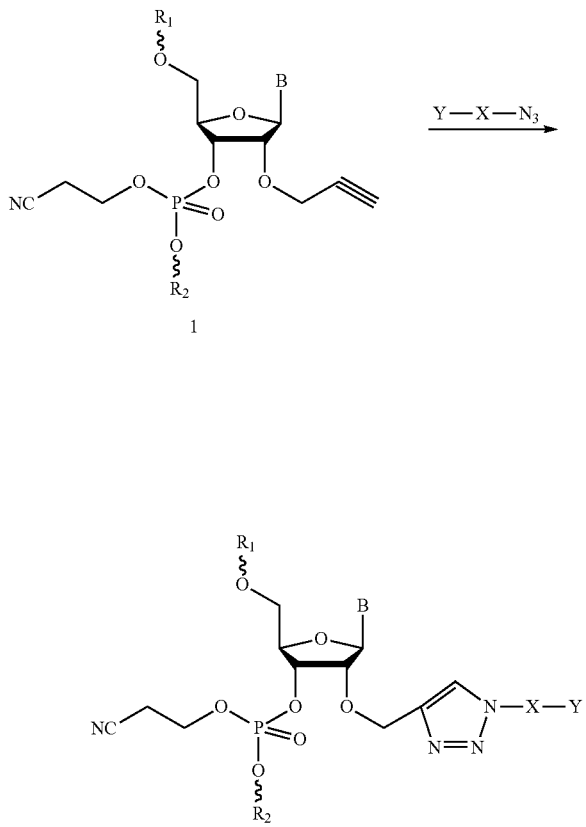

Scheme 1.

Where B is a nucleotide. If the nucleotide has a free amine group, it is preferably protected with an amine protecting group. Suitable amine protecting groups are described in T. W. Greene and P. G. M. Wuts "Protective Groups in Organic Synthesis" John Wiley & Sons, Inc., New York 1999, the entire teachings of which are incorporated herein by reference. Preferred amine protecting groups include benzoyl, acetyl, PAC, DMF, etc. Examples of protected nucleotides include A (N-Bz), C(N-Bz), C(N—Ac), G (N-iBu).

The alkynyl-substituted reactant can be an alkynyl-substituted oligonucleotide which is linked to a solid support, an oxo-substituted nucleotide, an alkynyl-substituted nucleoside, an alkynyl-substituted nucleoside phosphoramidite, or a composition (1): wherein R$_1$ is H, alkyl, or protecting group, such as those commonly used in oligonucleotide synthesis, e.g. dimethoxytrityl (DMT), monomethoxytrityl (MMT), or trityl, and R$_2$ is a linker used to attach an oligonucleotide to a solid support during synthesis of the oligonucleotide, such as the phosphate linkers. Suitably, X is aliphatic linker selected from group of substituted or unsubstituted, branched or unbranched hydrocarbons C$_1$-C$_{20}$. Y is a reporter molecule that includes, but is not limited to a fluorophore like pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compounds; as well as biotin, digoxigenin, peptides, proteins, antibodies, glycoproteins, and sugars.

The present method allows for multiple reporter moieties to be introduced into a single oligonucleotide. The reporter moieties may be the same or different. Use of different reporter moieties on a single oligonucleotide allows detection of multiple signals using a single oligonucleotide. Detection may be simultaneous or sequential.

The invention provides optimal conditions of cycloaddition reaction on solid support using corresponding catalysts (Table 1).

TABLE 1

| Cycloaddition reaction on solid support between fluorescein azide 3 and $T_{15}$-2'-propargyl-rU oligonucleotide resulting in SEQ ID NO 2. | |
|---|---|
| Catalyst | Coupling efficiency (reaction time—2 hrs) |
| $CuSO_4$/Sodium Ascorbate | 65% |
| $Cu(C_{10}H_{17}O_2)_2$/Sodium Ascorbate | 95% |
| $Pd[(C_6H_5)_3P]_4$ | 15% |
| $Ru(OAc)_2$(T-BINAP) | 21% |

The invention also provides novel azo compounds that are useful as fluorescence quenchers. The quenchers of this invention, which release energy absorbed from fluorophores without emitting light, i.e. are "dark quenchers", have the general formula shown below in Formula 3 (DG-2).

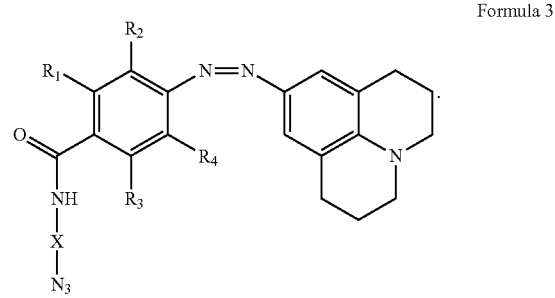

Formula 3

In Formula 3, each of $R_1$, $R_2$, $R_3$, and $R_4$ is independently an electron withdrawing group such as halogen, $NO_2$, $SO_3R$, $SO_2N(R)_2$, CN, CNS, keto, alkoxy, or $C_1$-$C_{10}$ alkyl, aryl, or heteroaryl. R is hydrogen or $C_1$-$C_{10}$ alkyl. In addition, the $R_1/R_2$ pair and $R_3/R_4$ can be combined to form condensed aromatic ring structures having five or six ring members. These ring structures can be optionally substituted with an electron withdrawing group such as halogen, $NO_2$, $SO_3R$, $SO_2N(R)_2$, CN, CNS, keto, alkoxy, or $C_1$-$C_{10}$ alkyl, aryl, or heteroaryl, where R is hydrogen or $C_1$-$C_{10}$ alkyl. X is an aliphatic linker $C_1$-$C_{20}$ between quencher molecule and reactive azide group.

Examples of other azidoalkyl substituted reporter moieties are shown in Schemes 2-3.

Scheme 2.

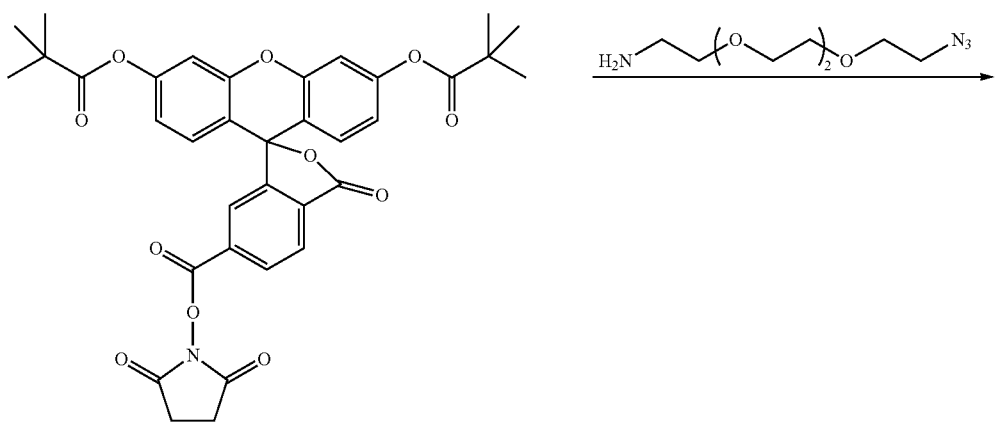

3

-continued

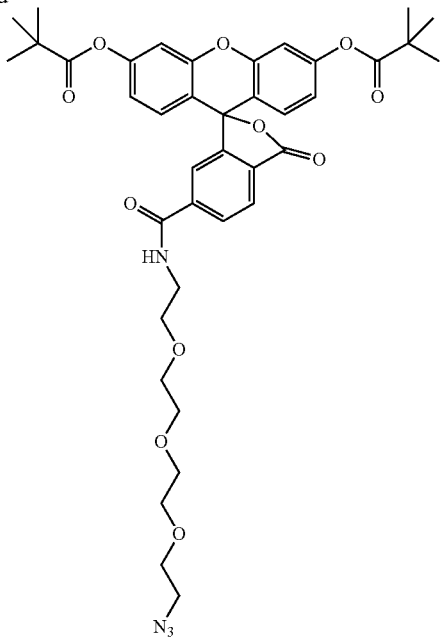

4

Scheme 3.

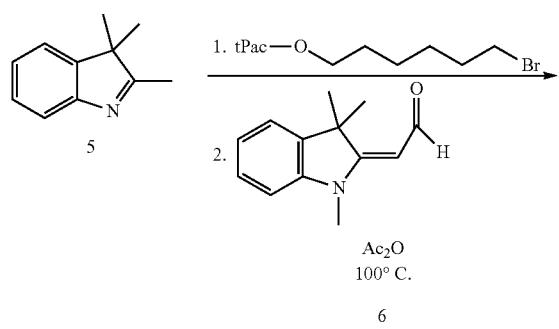

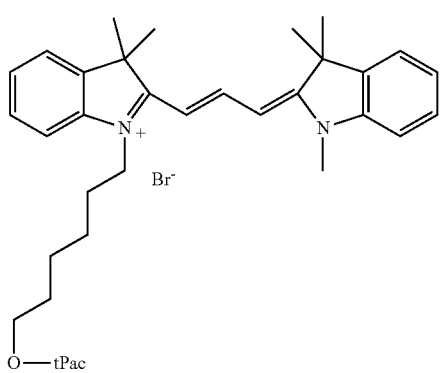

The invention also is directed to oligonucleotide compositions containing dye pairs, which include one of the disclosed quencher compounds and a fluorophore that fluoresces on exposure to light of the appropriate wavelength. Suitable fluorophores in the dye pair are those that emit fluorescence that can be quenched by the quencher of the dye pair. In certain embodiments, the dye pair can be attached to a single compound, such as an oligonucleotide. In other embodiments, the fluorophore and the quencher can be on different compounds.

A wide variety of reactive fluorophores are known in the literature and can be used with a corresponding quencher. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound. Suitable fluorophores include xanthene dyes, such as fluorescein or rhodamine dyes, including 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N;N'-tetramethyl-6-carboxyrhodamine (TAMRA), 6-carboxy-X-rhodamine (ROX). Suitable fluorophores also include the naphthylamine dyes that have an amino group in the alpha or beta position. For example, naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl)aminonaphthalene-1-sulfonic acid (EDANS). Other fluorophores include coumarins, such as 3-phenyl-7-isocyanatocoumarin; acridines, such as 9-isothiocyanatoacridine and acridine orange; N-(p-(2-benzoxazolyl)phenyl)maleimide; cyanines, such as indodicarbocyanine 3 (Cy3), indodicarbocyanine 5 (Cy5), indodicarbocyanine 5.5 (Cy5.5), 3-(-carboxy-pentyl)-3'-ethyl-5,5'-dimethyloxacarbocyanine (CyA); 1H,5H,11H,15H-Xantheno[2,3,4-ij:5,6,7i'j']diquinolizin-18-ium, 9-[2(or 4)-[[[6-[2,5-dioxo-1-pyrrolidinyl)oxy]-6-oxohexyl]amino]sulfonyl]-4(or 2)-sulfophenyl]-2,3,6,7, 12,13,16,17-octahydro-inner salt (TR or Texas Red); BODIPY dyes; benzoxaazoles; stilbenes; pyrenes; and the like.

The quencher of Formula 3 is capable of absorbing the fluorescent energy in the range of about 500 to about 530 m and therefore can be used to quench the fluorescence of fluorescein through Cy3.

Suitably, when the dye pair is in a configuration in which fluorophore is effectively quenched by the quencher dye, its fluorescence is reduced by at least a factor of 80%, and more preferably by 90%, 95%, or 98%, when compared to its fluorescence in the absence of quenching. High levels of quenching allow for the preparation of oligonucleotide probes having a high signal to noise ratio which is defined as the amount of signal present when the composition is in its maximal unquenched state (signal) versus its maximally quenched state (noise).

Probes having a high signal to noise ratio are desirable for the development of highly sensitive assays. To measure signal to noise ratios relative fluorescence is measured in a configuration where the quencher and fluorophore are within the Forster distance and the fluorophore is maximally quenched (background fluorescence or "noise") and compared with the fluorescence measured when fluorophore and quencher are separated in the absence of quenching ("signal"). The signal to noise ratio of a dye pair of the invention will generally be at least about 2:1 but generally is higher. Signal to noise ratios are generally affected by the fluorophore-quencher pair, the quality of the synthesis, and the oligonucleotide sequence.

Oligonucleotide probes that include a dye pair can be used to detect target oligonucleotides. In one method, the individual components of a dye pair can be on opposing, hybridizable, self-complementary segments of a single oligonucleotide such that when the oligonucleotide hybridizes to itself in the absence of exogenous sequences, FRET occurs. The oligonucleotide probe is constructed in such a way that the internal hybridizing is disrupted and fluorescence can be observed when the oligonucleotide probe hybridizes to a complementary target oligonucleotide. Such an oligonucleotide probe can be used to rapidly detect target oligonucleotides having sequences that bind to the oligonucleotide probe. In another embodiment, a composition comprises two biomolecules, such as oligonucleotides, with a fluorophore attached to one of the biomolecules and a quencher attached to the other.

The invention also provides kits that comprise a labeled oligonucleotide or an azo quencher of the present invention.

The kit can also contain instructions for use. Such kits can be useful for practicing the described methods or to provide materials for synthesis of the compositions as described. Additional components can be included in the kit depending on the needs of a particular method. For example, where the kit is directed to measuring the progress of PCR reactions, it can include a DNA polymerase.

The following examples further illustrate the invention but, of course, should not be construed as in any way limiting its scope. In particular the following examples demonstrate synthetic methods for obtaining the compounds of the invention. Starting materials useful for preparing the compounds of the invention and intermediates thereof, are commercially available or can be prepared from commercially available materials using known synthetic methods and reagents. All oligonucleotide sequences are written from the 5'-terminus on the left to the 3'-terminus on the right.

EXPERIMENTAL: EXAMPLES

Example 1

Synthesis of N-(dipivaloylfluorescein-6-ylcarbonyl)-1-amino-3,6,9-trioxaundecan-11-azide 4 as Shown in the Scheme 2

6-Carboxy-fluorescein dipivaloate was synthesized according to the procedure of F. M. Rossi et al (Bioconjugate Chem. 1997, 8, 495-497).

N-(dipivaloylfluorescein-6-ylcarbonyl)-1-amino-3,6,9-trioxaundecan-11-azide 4. To the solution of 1 g (1.8 mmol) of the 6-Carboxy-fluorescein dipivaloate and 0.25 g (2.2 mmol) of NHS in 10 mL of DMF were added 0.41 g (2.0 mmol) of DCC by one portion with stirring at room temperature. After 8 hrs the reaction mixture was filtered. To the resulting reaction mixture were added 0.32 mL (1.6 mmol) of 1-amino-3,6,9 trioxaundecan-1'-azide and 0.18 mL (1.3 mmol) of triethylamine and stirring continued at room temperature for another 4 hrs. The solvent was removed under diminished pressure and residue was extracted with 25 mL of ethyl acetate. Organic layer was combined, washed with 25 mL of brine and dried over anhydrous $Na_2SO_4$. Flash chromatography with 5:3:2 chloroform/hexanes/acetone provided 0.6 g (44.3%) of the compound 4. ESMS 767.8 $[C_{39}H_{44}N_4O_{11} (M+Na)^+$ requires 767.9].

Example 2

Synthesis of Julolidine-azo-(p-phenyl-carbonyl)-1-amino-3,6,9-trioxaundecan-11-azide Julolidine-azo-p-benzoic acid. To the solution of 1 g (7.3 mmol) of p-aminobenzoic acid in 5 mL of 20% aqueous HCl was added 3 ml of 5 M $NaNO_2$ aqueous solution dropwise with stirring at 0° C. After 10 min 0.16 g of urea were added slowly to the reaction mixture followed by the addition of 1.26 g (7.3 mmol) of julolidine in 2 mL of acetic acid. After 15 min the reaction mixture was quenched with 10 mL of 5 M aqueous NaOAc and stirring was continued for 1 hr at room temperature. The reaction mixture was extracted with two 25 mL portions of ethyl acetate and the organic layer was dried over $Na_2SO_4$. Flash chromatography provided 1.1 g (46.9%) of julolidine-azo-p-benzoic acid. ESMS 322.6 $[C_{19}H_{19}N_3O_2 (M+H)^+$ requires 322.4].

Julolidine-azo-p-phenylyl-carbonyl-1-amino-3,6,9-trioxaundecan-11-azide. To the solution of 200 mg (0.62 mmol) of julolidine-azo-p-benzoic acid and 117.4 μL (0.69 mmol) of DIPEA in 0.6 mL of acetonitrile were added 263.9 mg (0.69 mmol) of HBTU followed by addition of 186 μL (0.93 mmol) of 1-amino-3,6,9 trioxaundecan-11-azide with stirring at room temperature. After 12 hrs the reaction mixture was diluted with 3 mL of chloroform and washed with 5 mL of brine. The organic layer was separated and dried over anhydrous $Na_2SO_4$, Flash chromatography with 92:8 chloroform/methanol mobile system provided 205.0 mg (63.4%) of julolidine-azo-p-phenylyl-carbonyl-1-amino-3,6,9-trioxaundecan-11-azide. TLC $R_f$ 0.50 (8:92 MeOH-DCM). ESMS 532.6 [$C_{27}H_{35}N_7O_4$ $(M+H)^+$ requires 532.6].

Example 3

Synthesis of Cy3 Azide 8

2-[3-[1-(4-O-tert-butylphenoxyacetylhexyl)-1,3-dihydro-3,3-dimethyl-2H-indol-2-ylidene]-1-propenyl]-1,3,3-trimethyl-3H-indolium bromide (7). The solution of 0.5 g (3.14 mmol) of 2,3,3-trimethylindolenine and 1.16 g (3.14 mmol) of 6-bromohexyl-O-tert-butylphenoxyacetate in 2 mL of benzene was refluxed at 120° C. for 8 h. After cooling to room temperature, benzene was decanted and the oily residue was washed with two 5-mL portions of benzene. The crude product was used without purification. After dissolving the crude product in 8 mL of acetic anhydride, 0.632 g (3.14 mmol) of 2-(1,3,3-trimethylindolin-2-ylidene)acetaldehyde were added and the reaction was heated at 100° C. for 1 h. TLC showed the formation of a red fluorescent compound. After cooling to room temperature, acetic anhydride was removed under reduced pressure and the residue was applied to a silica gel column; elution with a gradient of 1:49-1:9 MeOH-DCM provided cyanine (7) as a red powder: Yield: 600 mg (35.2%). TLC $R_f$ 0.40 (1:19 MeOH-DCM). UV/Vis (buffer pH=11) $\lambda_{max}$ (nm) 559 ($\epsilon$=150,200 $M^{-1}$ $cm^{-1}$).

2-[3-[1-(6-hydroxyhexyl)-1,3-dihydro-3,3-dimethyl-2H-indol-2-ylidene]-1-propenyl]-1,3,3-trimethyl-3H-indolium bromide. To the solution of 0.5 g (6.2 mmol) of the compound 7 in 5 mL of methanol mixture were added 5 mL of concentrated ammonia in ethanol dropwise with stirring at 0-5° C. during the course of 15 min. The reaction mixture was warmed to room temperature. After 2 hrs the solvent was removed under diminished pressure. Flash chromatography provided 350 mg (88.1%) of 2-[3-[1-(6-hydroxyhexyl)-1,3-dihydro-3,3-dimethyl-2H-indol-2-ylidene]-1-propenyl]-1,3,3-trimethyl-3H-indolium bromide as red powder. ESMS 465.6 [$C_{30}H_{39}N_2O$ $(M+Na)^+$ requires 465.6].

2-[3-[1-(6-O-methylthiomethylhexyl)-1,3-dihydro-3,3-dimethyl-2H-indol-2-ylidene]-1-propenyl]-1,3,3-trimethyl-3H-indolium bromide. To a solution containing 350 mg (0.67 mmol) of 2-[3-[1-(6-hydroxyhexyl)-1,3-dihydro-3,3-dimethyl-2H-indol-2-ylidene]-1-propenyl]-1,3,3-trimethyl-3H-indolium bromide in 2 mL of DMSO, 2 mL of acetic acid and 1.5 mL of acetic anhydride were added. After stirring overnight, 5 mL of cold TEA was added dropwise and the reaction mixture was stirred for 15 min, then 10 mL of water was added and the aqueous layer was extracted with two 25-mL portions of dichloromethane. The organic layers were combined, dried over $Na_2SO_4$ and removed under reduced pressure. The residue was applied to a silica gel column; elution with a gradient of 1:49-1:9 MeOH-DCM provided 300 mg (76.8%) of 2-[3-[1-(6-O-methylthiomethylhexyl)-1,3-dihydro-3,3-dimethyl-2H-indol-2-ylidene]-1-propenyl]-1,3,3-trimethyl-3H-indolium bromide as a red powder. TLC $R_f$ 0.45 (1:19 MeOH-DCM). ESMS 525.6 [$C_{32}H_{43}N_2OS$ $(M+Na)^+$ requires 525.7].

Cy3 azide 8. To a solution containing 300 mg (0.51 mmol) of 2-[3-[1-(6-O-methylthiomethylhexyl)-1,3-dihydro-3,3-dimethyl-2H-indol-2-ylidene]-1-propenyl]-1,3,3-trimethyl-3H-indolium bromide in 6 mL of dichloromethane were added 0.6 mL of cyclohexene at room temperature with stirring. The reaction mixture was cooled to −20° C. and 47 μL (0.51 mmol) of $SO_2Cl_2$ were added with stirring during 5 min and reaction mixture was warmed to room temperature. After 2 hrs the solvent was removed under diminished pressure and a solution of 0.2 g (2.6 mmol) of sodium azide in 5 mL of dry DMF was added to the residue. After 2 hrs the solvent was removed under diminished pressure. The residue was applied to a silica gel column; elution with a gradient of 1:49-1:9 MeOH-DCM provided 75 mg (25.4%) of Cy3 azide 8 as a red powder. TLC $R_f$ 0.44 (1:19 MeOH-DCM). ESMS 520.3 [$C_{31}H_{40}N_5O$ $(M+Na)^+$ requires 520.7].

Example 4

Oligonucleotide Synthesis: To 30 mg of 2'-propargyl-Uridine CPG with 35 μmole/g loading were added 100 μL of 50 mM of corresponding azide in methanol 10 μL of 100 mM of aqueous sodium ascorbate solution and 1 μL of 100 mM of copper cyclohexanebutyrate solution in methanol. After 2 hrs the solid support was filtered and washed with 2 mL of acetonitrile. The resulting solid support was used further in oligonucleotide synthesis.

The following oligonucleotides (Table 2) were synthesized using 3'→5' directed standard phosphoramidite chemistry in 1 μmole scale.

TABLE 2

Oligonucleotide sequences with 2'-modifications attached via click chemistry.

| | |
|---|---|
| SEQ ID NO 1 | TTTTTTTTTrU2'-Ad |
| SEQ ID NO 2 | TTTTTTTTTTTTTrU2'-Fam |
| SEQ ID NO 3 | TTTTTTTTTTTTTrU2'-Cy3 |
| SEQ ID NO 4 | TTTTTTTTTTTTTrU2'-DG-2 |

Ad = Adamantane;

Fam = 6-carboxyfluorescein;

Cy3 = indodicarbocyanine 3;

DG-2 = Julolidine-azo-(p-phenyl-carbonyl)-1-amino-3,6,9-trioxaundecan-11-yl

Crude oligonucleotides were analyzed by CE and the identities of the oligonucleotides SEQ ID NO 1-4 were confirmed by ESI mass-spectrometry.

While this invention has been particularly shown and described with references to example embodiments thereof, it will be understood by those skilled in the art that various changes in form and details may be made therein without departing from the scope of the invention encompassed by the appended claims.

We claim:

1. A method for linking a reporter moiety to an oligonucleotide, comprising:

reacting a reporter moiety having an alkylazide group (Y—X—N₃) with an alkynyl substituted reactant (Z—W—C≡C—R₁) coupled to a solid support, thereby forming an azole-cycle represented by structural formula 4:

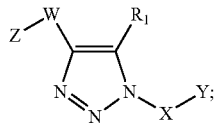

(Formula 4)

wherein

X is an aliphatic linker having a length of 1-20 atoms, where chain is comprised of carbon atoms, optionally substituted by one or more hetero atoms selected from the group consisting of nitrogen, oxygen and sulfur;

Y is reporter molecule;

W is a chain of atoms having a length of 1-20 atoms, where chain is comprised of carbon atoms, optionally substituted by one or more heteroatoms selected from the group consisting of nitrogen, oxygen and sulfur;

Z is controlled pore glass (CPG), polystyrene, or oligonucleotide chain attached to solid support; and R₁ is hydrogen or $C_1$-$C_{20}$ alkyl.

2. A method for linking a reporter moiety to an oligonucleotide attached to a solid support, comprising:

reacting a reporter moiety having an alkylazide group (Y—X—N₃) with an 2' alkynyl substituted reactant

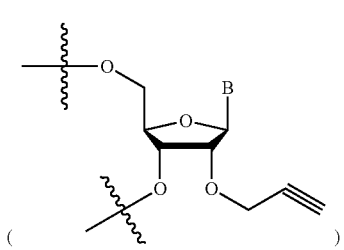

coupled to a solid support, forming an oligonucleotide comprising one or more reporter labeled nucleotides as represented by structural Formula 5:

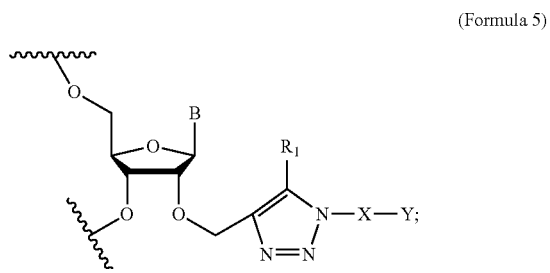

(Formula 5)

wherein:

one ∿∿ is an oligonucleotide attached to a solid support and other ∿∿ is at least one nucleotide, wherein the terminal nucleotide is protected with an alcohol protecting group (PG).

B is a nucleobase which is optionally functionalized at each primary amine with an amine protecting group;

R₁ is hydrogen or a $C_1$-$C_{20}$ alkyl;

X is an aliphatic linker having a length of 1-20 atoms, where chain is comprised of carbon atoms, optionally substituted by one or more hetero atoms selected from the group consisting of nitrogen, oxygen and sulfur; and Y is a reporter group.

3. A method for linking a reporter moiety to an oligonucleotide attached to a solid support, comprising:

reacting a reporter moiety having an alkylazide group (Y—X—N₃) with an 2' alkynyl substituted reactant

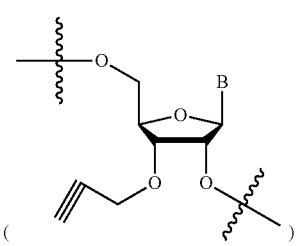

coupled to a solid support thereby forming the oligonucleotide comprising one or more reporter labeled nucleotides represented by structural formula 6:

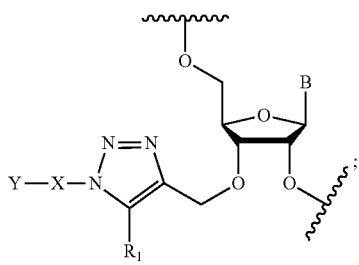

(Formula 6)

wherein:
one ∿∿ is an oligonucleotide attached to a solid support and other ∿∿ is at least one nucleotide, wherein the terminal nucleotide is protected with an alcohol protecting group (PG);
B is a nucleobase that is optionally functionalized at each primary amine with an amine protecting group;
$R_1$ is hydrogen or a $C_1$-$C_{20}$ alkyl;
X is an aliphatic linker having a length of 1-20 atoms, where chain is comprised of carbon atoms, optionally substituted by one or more hetero atoms selected from the group consisting of nitrogen, oxygen and sulfur; and
Y is a reporter group.

4. The method of claim 1, wherein reaction is catalyzed by $Pd[(C_6H_5)_3P]_4$ or $Ru(OAc)_2$(T-BINAP).

5. A compound represented by structural formula 7:

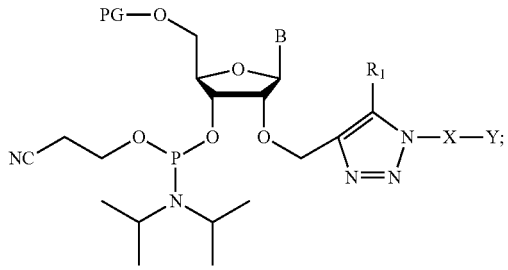

(Formula 7); or a salt thereof, wherein:
PG is an alcohol protecting group;
B is a nucleobase, which is optionally functionalized at each primary amine with an amine protecting group;
$R_1$ is hydrogen or a $C_1$-$C_{20}$ alkyl;
X is an aliphatic linker having a length of 1-20 atoms, where chain is comprised of carbon atoms, optionally substituted by one or more hetero atoms selected from the group consisting of nitrogen, oxygen and sulfur; and
Y is a reporter group.

6. The compound of claim 5, wherein:
B is an $N^6$-protected adenine, an $N^2$-protected guanine;
X is a $C_1$-$C_6$ straight aliphatic; and
Y is quencher, fluorophore, biotin, digoxigenin, ferrocene, peptide, protein, antibody, glycoprotein, polyethylene glycol (PEG), lipid or sugar.

7. The compound of claim 6, wherein B is $N^6$-benzoyl adenine or $N^2$-isobutryl guanine.

8. The compound of claim 5 wherein PG is trityl, dimethoxytrityl, monomethoxytrityl, tert-butyldimethylsilyl or 2-(2-nitrophenyl)propoxycarbonyl.

9. A compound represented by structural formula 3:

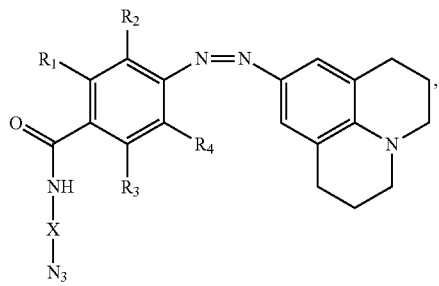

(Formula 3); wherein
each of $R_1$, $R_2$, $R_3$, and $R_4$ is independently selected from the group consisting of halogen, $NO_2$, $SO_3R$, $SO_2N(R)_2$, CN, CNS, $C(=O)C_1$-$C_{20}$ alkyl, alkoxy, $C_1$-$C_{20}$ alkyl, aryl groups and heteroaryl; or
$R_1$ and $R_2$ together with their intervening atoms and/or $R_3$ and $R_4$ together with their intervening atoms form an optionally substituted five to six membered ring, wherein either ring formed is optionally substituted with halogen, $NO_2$, $SO_3R$, $SO_2N(R)_2$, CN, CNS, $C(=O)C_1$-$C_{20}$, alkoxy, $C_1$-$C_{20}$ alkyl, aryl groups and heteroaryl;
R is hydrogen or $C_1$-$C_{20}$ alkyl; and
X is an aliphatic linker having a length of 1-20 atoms, where chain is comprised of carbon atoms, optionally substituted by one or more hetero atoms selected from the group consisting of nitrogen, oxygen and sulfur.

10. An oligonucleotide attached to a solid support, wherein the oligonucleotide comprises one or more reporter labeled nucleotides and is represented by structural formula 5 or structural formula 6:

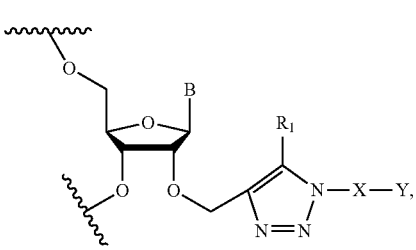

(Formula 5)

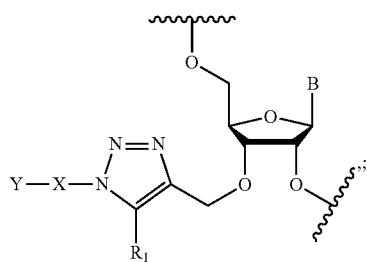

(Formula 6)

wherein:
one ∿∿ is an oligonucleotide attached to a solid support and other ∿∿ is at least one nucleotide, wherein the terminal nucleotide is protected with an alcohol protecting group (PG);
B is a nucleobase which is optionally functionalized at each primary amine with an amine protecting group;
$R_1$ is hydrogen or a $C_1$-$C_{20}$ alkyl;

X is an aliphatic linker having a length of 1-20 atoms, where chain is comprised of carbon atoms, optionally substituted by one or more hetero atoms selected from the group consisting of nitrogen, oxygen and sulfur; and Y is a reporter group.

11. The oligonucleotide of claim 10, wherein each reporter group in the oligonucleotide is different.

12. The oligonucleotide of claim 10 the labeling efficiency at each labeled nucleotide is at least 90%, preferably 95% and more preferably 99%.

13. The oligonucleotide of claim 10, wherein:
B is an $N^6$-protected adenine or an $N^2$-protected guanine;
X is an aliphatic linker having a length of 1-20 atoms, where chain is comprised of carbon atoms, optionally substituted by one or more hetero atoms selected from the group consisting of nitrogen, oxygen and sulfur; and
Y is a quencher, fluorophore, biotin, digoxigenin, ferrocene, peptide, protein, antibody, glycoprotein, polyethylene glycol (PEG), lipid or sugar.

14. The oligonucleotide of claim 13, wherein B is $N^6$-benzoyl adenine or $N^2$-isobutryl guanine 15. The oligonucleotide of claim 10 wherein PG is trityl, dimethoxytrityl, monomethoxytrityl, tert-butyldimethylsilyl or 2-(2-nitrophenyl)propoxycarbonyl.

16. A composition comprising a plurality of oligonucleotides, wherein:
the nucleotide sequence of each oligonucleotide in the plurality is the same;
at least 90% of the oligonucleotides in the plurality are labeled at the same nucleotide in the olignonucleotide sequence with a reporter group, each reporter group being the same; and
the reporter labeled nucleotide is represented by a structural formula selected from:

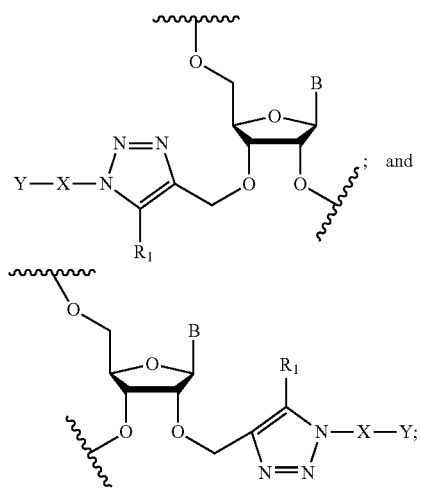

wherein:
one ⌇ in each of the above structural formula is an oligonucleotide attached to a solid support and other ⌇ in each of the above structural formula is at least one nucleotide, wherein the terminal nucleotide is protected with an alcohol protecting group (PG);
each B is a nucleobase which is optionally functionalized at each primary amine with an amine protecting group;
each $R_1$ is hydrogen or a $C_1$-$C_{20}$ alkyl;
each X is an aliphatic linker having a length of 1-20 atoms, where chain is comprised of carbon atoms, optionally substituted by one or more hetero atoms selected from the group consisting of nitrogen, oxygen and sulfur; and
each Y is a reporter group.

17. The composition of claim 16 wherein:
at least 90% of the oligonucleotides in the plurality comprise a second nucleotide labeled with a reporter group, wherein said second nucleotide is the same nucleotide in each of the oligonucelotide sequence with a second labeled nucleotide and is represented by a structural formula selected from:

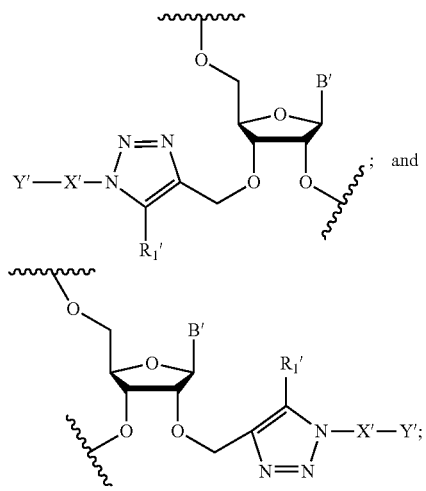

wherein:
one ⌇ in each of the above structural formula is an oligonucleotide attached to a solid support and other ⌇ in each of the above structural formula is at least one nucleotide, wherein the terminal nucleotide is protected with an alcohol protecting group (PG);
each B' is an $N^6$-protected adenine, an $N^2$-protected guanine;
each $R_{1'}$ is hydrogen or a $C_1$-$C_{20}$ alkyl group;
each X' is a $C_1$-$C_6$ straight aliphatic group;
Y' is quencher, fluorophore, biotin, digoxigenin, ferrocene, peptide, protein, antibody, glycoprotein, polyethylene glycol (PEG), lipid or sugar; and
X and X' are the same or different; Y and Y' are the same or different; and B and B' are the same or different.

18. The composition of claim 17 further comprising a second oligonucleotide, wherein the nucleotide sequence of the second oligonucletide is different from the nucleotide sequence of the plurality of the reporter labeled oligonucelotides; and/or wherein the second oligonucleotide is labeled at a different position of its nucleotide sequence with reporter groups as compared to the plurality of the reporter labeled oligonucleotides.

19. The composition of claim 16, wherein B is $N^6$-benzoyl adenine or $N^2$-isobutryl guanine.

20. The composition of claim 17 wherein PG is trityl, dimethoxytrityl, monomethoxytrityl, tert-butyldimethylsilyl or 2-(2-nitrophenyl) propoxycarbonyl.

21. A method of preparing an oligonucleotide labeled with a reporter group, wherein said reporter labeled oligonucelotide comprises a reporter labeled nucleotide represented by a structural formula selected from:

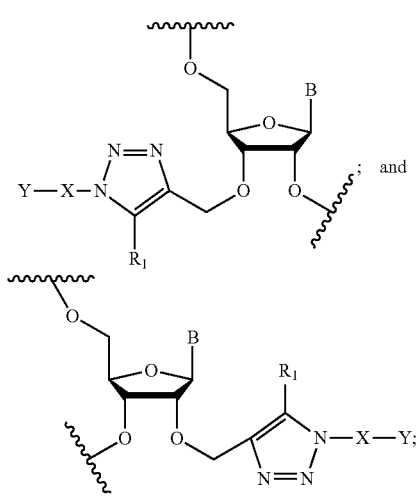

said method comprises the step of reacting a compound represented by Y—X—N$_3$ with a propargyl labeled oligonucelotide; wherein the propargyl labeled oligonucelotide comprises a propargyl labeled nucleotide represented by a structural formula selected from:

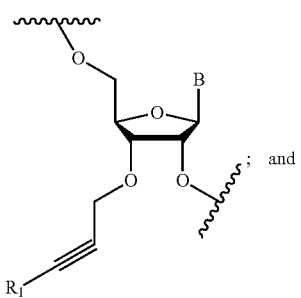

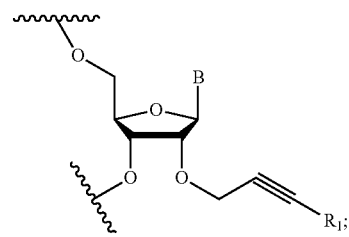

wherein:

one ∿∿∿ in each of the above structural formula is an oligonucleotide attached to a solid support and other ∿∿∿ in each of the above structural formula is at least one nucleotide, wherein the terminal nucleotide is protected with an alcohol protecting group (PG);

B is a nucleobase which is optionally functionalized at each primary amine with an amine protecting group;

R$_1$ is hydrogen or a C$_1$-C$_{20}$ alkyl;

X is an aliphatic linker having a length of 1-20 atoms, where chain is comprised of carbon atoms, optionally substituted by one or more hetero atoms selected from the group consisting of nitrogen, oxygen and sulfur; and Y is a reporter group. thereby forming the reporter labeled oligonucleotide;

wherein the propargyl and reporter labeled oligonucleotides are linked to a solid support, and/or the labeling efficiency at the propargyl labeled nucleotide is at least 90%, preferably 95% and more preferably 99%.

* * * * *

SEQUENCE LISTING

<160> NUMBER OF SEQ ID NOS: 4

<210> SEQ ID NO 1
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 10
<223> OTHER INFORMATION: u at position 10 is uracil ribonucleic acid
<220> FEATURE:
<221> NAME/KEY: misc_feature
<222> LOCATION: 10
<223> OTHER INFORMATION: Uracil at position 10 is modified by Adamantane
    (Ad) attached to the nucleotide at 2' end

<400> SEQUENCE: 1
tttttttttu                                                          10

<210> SEQ ID NO 2
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 15
<223> OTHER INFORMATION: u at position 15 is uracil ribonucleic acid
<220> FEATURE:
<221> NAME/KEY: misc_feature
<222> LOCATION: 15
<223> OTHER INFORMATION: Uracil at position 15 is modified by
    6-carboxyfluorescein (FAM) attached to the
    nucleotide at 2' end

<400> SEQUENCE: 2
tttttttttt ttttu                                                    15

<210> SEQ ID NO 3
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 15
<223> OTHER INFORMATION: u at position 15 is uracil ribonucleic acid
<220> FEATURE:
<221> NAME/KEY: misc_feature
<222> LOCATION: 15
<223> OTHER INFORMATION: Uracil at position 15 is modified by
    indodicarbocyanine 3 (Cy3) attached to the
    nucleotide at 2' end

<400> SEQUENCE: 3
tttttttttt ttttu                                                    15

<210> SEQ ID NO 4
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 15
<223> OTHER INFORMATION: u at position 15 is uracil ribonucleic acid

```
<220> FEATURE:
<221> NAME/KEY: misc_feature
<222> LOCATION: 15
<223> OTHER INFORMATION: Uracil at position 15 is modified by
      Julolidine-azo-(p-phenyl-carbonyl)-1-amino-3,6,9-
      trioxaundecan-11-yl (DG-2) attached to the
      nucleotide at 2' end

<400> SEQUENCE: 4
tttttttttt ttttu                                              15
```